(12) United States Patent
Ramin

(10) Patent No.: US 6,726,916 B1
(45) Date of Patent: *Apr. 27, 2004

(54) THICKENED FILM-FORMING COMPOSITION

(75) Inventor: Roland Ramin, Paris (FR)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 444 days.

(21) Appl. No.: 09/141,515

(22) Filed: Aug. 27, 1998

(30) Foreign Application Priority Data

Aug. 28, 1997 (FR) .............................. 97 10759

(51) Int. Cl.$^7$ .............. A61K 6/00; A61K 9/14; A61K 7/04; A61K 47/00; A61K 47/32
(52) U.S. Cl. .......... 424/401; 424/488; 424/61; 514/782; 514/777; 514/772.6
(58) Field of Search ............ 424/488, 61, 401, 424/78.02, 78.03; 514/782, 777, 772.6

(56) References Cited

U.S. PATENT DOCUMENTS

| | | | |
|---|---|---|---|
| 5,071,639 A | 12/1991 | Soyama et al. | 424/61 |
| 5,612,021 A | 3/1997 | Mellul | 424/61 |
| 5,650,159 A | 7/1997 | Lion et al. | 424/401 |
| 5,833,967 A | * 11/1998 | Ramin | 424/70.4 |
| 5,872,246 A | 2/1999 | Commander et al. | 536/124 |

FOREIGN PATENT DOCUMENTS

| | | | |
|---|---|---|---|
| DE | 195 22 750 | 1/1997 | |
| EP | A 281 360 | 9/1988 | |
| EP | A 455 073 | 11/1991 | |
| EP | A 651 990 | 5/1995 | |
| EP | A 705 592 | 4/1996 | |
| EP | 0708114 A | * 4/1996 | |
| EP | A 708 114 | 4/1996 | |
| EP | 0 745 372 A1 | 12/1996 | |
| EP | A 776 654 | 6/1997 | |
| EP | A 776 665 | 6/1997 | |
| FR | 1 453 089 | 9/1966 | |
| FR | 2 734 718 | 12/1996 | |
| FR | 2 734 719 | 12/1996 | |
| FR | 2 734 722 | 12/1996 | |
| GB | 2 021 411 | 12/1979 | |
| JP | 8-333222 | 12/1996 | |
| JP | A-09-151125 | 6/1997 | |
| WO | 94 18935 | 9/1994 | |
| WO | 96 02225 | 2/1996 | |
| WO | WO 96/23482 | 8/1996 | A61K/7/06 |

OTHER PUBLICATIONS

Research Disclosure, No. 38413, pp. 235–236, XP–002067847, Clarke et al. Ethyl galactomannan film properties for use in personal care applications, Hercules Inc., 1996.*
English Language Derwent Abstract of RD 95 378 007.
Majewicz et al., "Oil–Based Cosmetic and Therapeutic Compositions Containing Ethylguar", Research Disclosure, No. 37807, p. 642, XP–002067837, Oct. 1995, Hercules Incorporated.
Clarke et al., "Ethyl Galactomannan Film Properties For Use In Personal Care Applications", Research Disclosure, No. 38413, pp. 235–236, XP–002067847, Apr. 1996, Hercules Incorporated.
English Language Derwent Abstract of DE 195 22 750.
English Language Derwent Abstract of EP A 651 990.
English Language Derwent Abstract of EP A 705 592.
English Language Derwent Abstract of EP A 776 665.
English Language Derwent Abstract of FR 1 453 089.

* cited by examiner

Primary Examiner—Theodore J. Criares
(74) Attorney, Agent, or Firm—Finnegan, Henderson, Farabow, Garrett & Dunner LLP

(57) ABSTRACT

A thickened film-forming composition comprising a film-forming polymer and, as thickener, a polysaccharide alkyl ether formed of units containing at least two different saccharide rings, each unit containing at least one hydroxyl group substituted with a saturated hydrocarbon-based alkyl chain. The polysaccharide alkyl ether preferably has a molecular weight of greater than 200,000 and is in particular a guar gum alkyl ether having a degree of substitution of from about 2 to 3, in particular 2.5. The composition can be used in particular in the cosmetics fields for keratinous materials, especially the nails.

37 Claims, No Drawings

THICKENED FILM-FORMING COMPOSITION

Applicant references herein the patent applications of PASCAL ARNAUD for THICKENED COMPOSITION COMPRISING FUSED SILICA and ROLAND RAMIN and PASCAL ARNAUD for MAKE-UP REMOVING COMPOSITION filed on even date herewith and incorporates the disclosures thereof specifically by reference herein.

The invention relates to a film-forming composition comprising a film-forming polymer and a novel thickener which can be used in the cosmetics field. The invention also relates to a use of this composition for the treatment and care of keratinous material such as the skin, the nails, the eyelashes, the eyebrows, the hair or mucous membranes such as the lips and the inside of the eyelids. It is intended more especially for treating and caring for the nails.

More specifically, the invention relates to a composition containing film-forming polymers, which is capable of forming a homogeneous, continuous film on a support (nail, eyelash or hair).

In film-forming compositions such as nail varnishes, it is common to thicken the organic phase with thickeners. The thickened compositions make it easier to take the product from its packaging without any significant loss, to distribute the product uniformly over the area to be treated, or alternatively to be able to use the product in sufficient amounts to obtain the desired cosmetic effect. Furthermore, for compositions comprising an amount of pigments such as nail varnishes, the thickener prevents sedimentation of the pigments during storage.

To thicken compositions, it is known to use clays such as the organomodified montmorillonites, as described in British patent application GB-A-2,021,411. However, the preparation of such compositions requires the clay to be well dispersed in the composition. Thus, the dispersion must necessarily be carried out using a Gaulin high-pressure homogenizer, which entails a restricting, long and expensive step in the manufacture of the compositions. It is thus desirable to have available a thickener which is easy to use. In addition, clays such as organomodified montmorillonites modify the properties of the film obtained when the composition is applied, since it is observed that the film has less impact strength and becomes chipped more easily.

Hydrophilic and hydrophobic silicas are also known as thickeners in nail varnishes, in particular in French patent application FR-A-1,453,089. Although silicas do not harm the properties of the film obtained once the composition is applied, they are, however, difficult to use, thus necessitating a step of placing in dispersion. Furthermore, silicas have a tendency to give a matte effect to the film-forming composition and the film obtained, leading to the formation of matte or satin films. They are thus not recommended for use for the preparation of transparent film-forming compositions and for the production of a shiny film.

An aim of the present invention is to provide a thickened, transparent, film-forming composition which is well-suited to nail care, which has good cosmetic properties and which does not have the drawbacks mentioned above.

The inventor has discovered that such a composition can be obtained by using a specific thickener.

A subject of the present invention is thus a composition comprising a film-forming polymer and an organic phase, characterized in that it comprises a polysaccharide alkyl ether formed of units containing at least two different saccharide rings, each unit containing at least one hydroxyl group substituted with a saturated hydrocarbon-based alkyl chain, the organic phase comprising at least one medium which is a solvent for the polysaccharide alkyl ether.

By virtue of the polysaccharide alkyl ether, the composition according to the invention is transparent and has a satisfactory viscosity which allows good spreading of the composition. This thickener is entirely suitable for the preparation of pigmented compositions that are stable over time, such as nail varnishes.

In the thickener of the invention, the term "hydrocarbon-based alkyl chain" is understood to refer to a linear or branched chain preferably containing from 1 to 24, more preferably from 1 to 10, better still from 1 to 6 and more especially from 1 to 3, carbon atoms. In particular, the alkyl chain is selected from ethenyl and propenyl and preferably from saturated chains and in particular methyl, ethyl, n-propyl, isopropyl, n-butyl, isobutyl, tert-butyl and n-pentyl. These alkyl ethers can be manufactured as described in documents EP-A-281,360 and EP-A-708,114, the disclosures of which are specifically incorporated herein by reference.

According to a preferred embodiment of the invention, the polysaccharide alkyl ether has a weight-average molecular weight of greater than 100,000, and preferably greater than 200,000. This molecular weight can be up to 1 million. This alkyl ether preferably contains from 1 to 6, and better still from 2 to 4, hydroxyl groups per unit, substituted with a saturated or unsaturated hydrocarbon-based alkyl chain.

The saccharide rings are selected in particular from mannose, galactose, glucose, furanose, rhamnose and arabinose.

According to a preferred embodiment of the invention, the polysaccharide alkyl ether is an alkyl ether of a gum and more particularly of a gum which is nonionic overall, i.e. one which contains few or no ionic groups. As appropriate gums, mention may be made, for example, of guar gum, in which the unit comprises a galactose and a mannose, carob gum, in which the unit comprises a galactose and a mannose, karaya gum, which is a complex mixture of rhamnose, galactose and galacturonic acid, and gum tragacanth, which is a complex mixture of arabinose, galactose and galacturonic acid.

According to a preferred embodiment of the invention, the polysaccharide alkyl ether is a guar gum derivative. Thus, advantageously, the alkyl ether is an alkyl galactomannan with a $C_1$ to $C_6$, and better still $C_1$ to $C_3$, alkyl chain and more particularly ethyl guar having a degree of substitution of from 2 to 3 and in particular from about 2.5 to 2.8, as described in the documents RD 95378007 (October 1995) and EP-A-708,114, the disclosures of which are specifically incorporated by reference herein. This gum is sold in particular by the company Aqualon under the names N-HANCE-AG 200® and N-HANCE AG 50®.

The concentration of alkyl ether depends on the pharmaceutical form and the consistency desired for the composition, as well as on the amount of organic phase to be thickened. In particular, the weight ratio of the amount of liquid fatty phase to the amount of thickener is selected, for example, preferably in the range from 5 to 500. The composition according to the invention can contain, for example, an amount of polysaccharide alkyl ether preferably ranging from 0.2 to 20% of the total weight of the composition, and more preferably from 1.5 to 8%.

According to the invention, the medium which is a solvent for the polysaccharide alkyl ether present in the composition can be an organic solvent or an oil. In other words, the polysaccharide alkyl ether is a thickener for the organic solvents and the oils. The term oils is understood to refer to any fatty substance which is liquid at room temperature.

The organic solvent can be selected, for example, from:

ketones that are liquid at room temperature, such as methyl ethyl ketone, methyl isobutyl ketone, diisobutyl ketone, isophorone, cyclohexanone and acetone;

alcohols that are liquid at room temperature, such as ethanol, isopropanol, diacetone alcohol, 2-butoxyethanol and cyclohexanol;

glycols that are liquid at room temperature, such as ethylene glycol, propylene glycol and pentylene glycol;

propylene glycol ethers that are liquid at room temperature, such as propylene glycol monomethyl ether, propylene glycol monomethyl ether acetate and dipropylene glycol mono-n-butyl ether;

esters with a short chain, (having from 3 to 8 carbon atoms in total), such as ethyl acetate, methyl acetate, propyl acetate, n-butyl acetate and isopentyl acetate;

ethers that are liquid at room temperature, such as diethyl ether, dimethyl ether and dichlorodiethyl ether;

alkanes that are liquid at room temperature, such as decane, heptane, dodecane and cyclohexane;

aromatic cyclic compounds that are liquid at room temperature, such as toluene and xylene;

aldehydes that are liquid at room temperature, such as benzaldehyde and acetaldehyde.

These solvents are more particularly suitable for making up and caring for nails: in this case, the composition constitutes a nail varnish or a nail care product.

Among the oils which can be used as a medium which is a solvent for the polysaccharide alkyl ether according to the invention, mention may be made, for example, of:

oils of plant origin, such as liquid triglycerides, for example sunflower oil, corn oil, soybean oil, jojoba oil, marrow oil, grapeseed oil, sesame oil, hazelnut oil, apricot oil, macadamia oil, castor oil, caprylic/capric acid triglycerides such as those sold by the company Stearineries Dubois or those sold under the names MIGLYOL 810, 812 and 818 by the company Dynamit Nobel;

oils of animal origin, such as lanolin;

oils of mineral origin;

synthetic oils, for instance fatty alcohols such as 2-octyldodecanol; esters, and in particular fatty acid esters, especially esters having a total number of carbon atoms ranging from 12 to 80 and better still from 16 to 50; phenylsilicones and in particular phenyltrimethicones, diphenyldimethicones and polymethylphenylsiloxanes.

A person skilled in the art will know, on the basis of his or her knowledge, how to determine, by simple routine tests, the oils which are solvents for the polysaccharide alkyl ether.

These oils which are solvents for the polysaccharide alkyl ether are more particularly suitable for the preparation of nail care products.

Complementary oils that are not solvents for the polysaccharide alkyl ether can also be added to the composition. As complementary oil, mention may be made in particular of silicone gums and resins that are liquid at room temperature, partially fluorinated hydrocarbon-based oils, perfluoro oils, silicone oils free of aromatic groups, such as linear or branched polysiloxanes, for instance polydimethylpolysiloxanes, polyethylmethylpolysiloxanes, polyalkylmethylsiloxanes and cyclic polysiloxanes such as octamethylcyclotetrasiloxane and decamethylcyclopentasiloxane or mixtures thereof; fluorosilicone oils; polysiloxanes functionalized with one or more hydroxyl functions and/or one or more polyether groups, such as dimethicone copolyols; linear or branched hydrocarbons, for instance liquid petroleum jelly, isohexadecane and isododecane.

The solvents for the polysaccharide alkyl ether (organic solvent or oil) can be present in a proportion preferably ranging from 40 to 99.3% by weight, relative to the total weight of the organic phase of the composition, and better still from 72% to 98.5%. The complementary oils can be added to the composition in an amount which can preferably range from 0% to 75% by weight, relative to the total weight of the organic phase, and better still from 0% to 50% by weight.

The film-forming polymer present in the composition according to the invention can be any polymer commonly used in nail varnishes in a solvent medium, which is well known to those skilled in the art. For example, the polymer can be selected from nitrocellulose, cellulose acetobutyrate, polyvinyl butyrals, alkyd resins, the resins resulting from the condensation of formaldehyde with an arylsulphonamide, polyesters, polyurethanes, polyesterpolyurethanes, polyetherpolyurethanes, radical polymers, in particular of the acrylic, styreneacrylic and/or vinylic type, and mixtures thereof.

The polymers can be dissolved or dispersed in the composition. They can generally be present in a content preferably ranging from 0.5% to 40% by weight relative to the total weight of the composition, and better still ranging from 10% to 20% by weight.

By virtue of the presence of the polysaccharide alkyl ether, it is possible to use, in combination fumed silica, in particular in order to adjust the viscosity of the composition, without harming the film's sheen.

The fumed silica can be in the form of hydrophilic fumed silica or hydrophobic fumed silica.

The fumed silicas can be obtained by high-temperature hydrolysis of a volatile silicon compound in an oxyhydrogen flame, producing a finely divided silica. This process makes it possible in particular to obtain hydrophilic silicas which have a large number of silanol groups at their surface. Such hydrophilic silicas are sold, for example, under the names "AEROSIL 130®", "AEROSIL 200®", "AEROSIL 255®", "AEROSIL 300®", "AEROSIL 380®" by the company Degussa and "CAB-O-SIL HS-5®", "CAB-O-SIL EH-5®", "CAB-O-SIL LM-130®", "CAB-O-SIL MS-55®", "CAB-O-SIL M-5®" by the company Cabot.

It is possible to chemically modify the surface of the silica, by chemical reaction generating a decrease in the number of silanol groups. In particular, silanol groups can be substituted with hydrophobic groups: a hydrophobic silica is then obtained.

The hydrophobic groups can be:

trimethylsiloxyl groups, which are obtained in particular by treatment of fumed silica in the presence of hexamethyidisilazane. Silicas thus treated are known as "silica silylate" according to the CTFA (6th edition, 1995). They are sold, for example, under the references "AEROSIL R812®" by the company Degussa and "CAB-O-SIL TS-530®" by the company Cabot;

dimethylsilyloxyl or polydimethylsiloxane groups, which are obtained in particular by treatment of fumed silica in the presence of polydimethylsiloxane or dimethyidichlorosilane. Silicas thus treated are known as "silica dimethyl silylate" according to the CTFA (6th edition, 1995). They are sold, for example, under the references "AEROSIL R972®", "AEROSIL R974®" by the company Degussa, "CAB-O-SIL TS-610®" and "CAB-O-SIL TS-720®", by the company Cabot.

The fumed silica preferably has a particle size which can be nanometric to micrometric, for example preferably ranging from approximately 5 to approximately 200 nm.

The fumed silica can be present in the composition according to the invention in an amount preferably ranging from 0.1% to 5% by weight, relative to the total weight of the organic phase of the composition, more preferably from 0.5% to 1% by weight.

It is also possible to introduce a clay such as organomodified bentonites into the composition, without harming the property of the film, by virtue of the presence of the polysaccharide alkyl ether. This clay can be present in an amount preferably ranging from 0.1% to 3% by weight, relative to the total weight of the composition, and better still from 0.5% to 1.5% by weight. As bentonites, use may be made of those sold under the names "BENTONE 27®", "BENTONE 34®" AND "BENTONE 38®", by the company Rheox, or alternatively under the name "TIXOGEL LG®" by the company Sud Chemie.

The composition according to the invention can also comprise, in addition to the film-forming polymer, plasticizers which allow the film's flexibility to be adjusted without weakening its physical strength.

The plasticizers which can be used are those commonly employed in nail varnish compositions. As plasticizers, mention may be made of dibutyl phthalate, dioctyl phthalate, diisobutyl phthalate, dimethoxyethyl phthalate, benzyl benzoate, glyceryl benzoate; triethyl citrate, tributyl citrate, tributyl acetyl citrate; tributyl phosphate, triphenyl phosphate; glycols; camphor, as well as their derivatives and their mixtures. The plasticizers can generally be present in a content preferably ranging from 1% to 30% by weight relative to the total weight of the composition, and better still from 5% to 10% by weight.

Moreover, the composition according to the invention can contain adjuvants commonly used in cosmetic compositions. As examples of adjuvants, mention may be made of dyes, pigments, pearlescent agents, lakes, anti-UV agents, thickeners, surfactants, waxes, fragrances, active agents such as D-panthenol, phytanetriol, vitamins and their derivatives, keratin and its derivatives, melanin, collagen, cystine, chitosan, and its derivatives, biotin, trace elements, glycerol, protein hydrolysates, phospholipids and moisturizers. Needless to say, a person skilled in the art will take care to select this or these optional adjuvants, and/or the amount thereof, such that the advantageous properties of the composition according to the invention are not, or are not substantially, adversely affected by the addition envisaged.

The composition according to the invention can advantageously be used to treat, make up or care for keratinous material and/or mucous membranes depending on the nature of the active agents used. The composition of the make-up can be a nail varnish, an eyeliner, a mascara, a foundation, a concealer, an eyeshadow, a blusher, or a lipstick.

The composition according to the invention can advantageously be in the form of a nail varnish or a nail care composition. Thus, the subject of the invention is also a nail care or nail varnish composition comprising a film-forming polymer, an organic phase and a polysaccharide alkyl ether as defined above.

The invention also relates to the use of a polysaccharide alkyl ether, as defined above, as a thickener for a composition containing a film-forming polymer and an organic phase comprising at least one medium which is a solvent for the said alkyl ether.

The invention also relates to a cosmetic process for treating or making up keratinous material, and in particular the nails and/or mucous membranes, this process involving applying a composition as described above to the keratinous material and/or the mucous membranes.

Examples illustrating the present invention without, however, limiting it will now be given.

EXAMPLE 1

A nail varnish composition having the following composition was prepared:

| | |
|---|---|
| - Film-forming polymers (nitrocellulose, alkyd resin) | 28 g |
| - Plasticizer | 7 g |
| - Isopropyl alcohol | 5 g |
| - Ethyl guar with a degree of substitution of about 2.5 (1) | 3 g |
| - Pigments | 1 g |
| - Ethyl acetate/butyl acetate qs | 100 g |

(1) Sold under the name N-HANCE AG 200® by Aqualon

After applying the composition to the nail and drying, a smooth, homogeneous, shiny film was obtained.

EXAMPLE 2

A nail care product having the following composition was prepared:

| | |
|---|---|
| - Film-forming polymers (nitrocellulose, alkyd resin) | 14 g |
| - Plasticizer | 3 g |
| - UV screening agent | 0.5 g |
| - Dyes | 0.1 g |
| - Fumed silica (Degussa 200) | 0.5 g |
| - Isopropanol | 5 g |
| - Ethyl guar with a degree of substitution of about 2.5 (1) | 0.5 g |
| - D-Panthenol | 0.5 g |
| - Phytanetriol | 0.1 g |
| - Butyl acetate/ethyl acetate qs | 100 g |

(1) Sold under the name N-HANCE AG 200® by Aqualon

The composition applied easily to the nails and, after drying, left a homogeneous, shiny film which enhances the state of the nails.

EXAMPLE 3

A nail care oil having the following composition was prepared:

| | |
|---|---|
| - Cellulose acetobutyrate | 0.5 g |
| - Mineral oil | 5 g |
| - Fumed silica (Degussa 200) | 0.5 g |
| - Ethyl guar with a degree of substitution of about 2.5 (1) | 0.5 g |
| - Additives (active agents and dyes) | 1 g |
| - Isopropyl alcohol | 5 g |
| - Propylene glycol monomethyl ether | 3 g |
| - Volatile silicone oil | 20 g |
| - Plant oil qs | 100 g |

(1) Sold under the name N-HANCE AG 200® by Aqualon

This care oil applied easily to the nails and the cuticles; it penetrated into the nail matrix and into the nail bed by massaging.

I claim:

1. A nonaqueous cosmetic composition comprising at least one film-forming polymer and an organic phase comprising at least one polysaccharide alkyl ether formed of units containing at least two different saccharide rings, wherein each unit contains at least one hydroxyl group substituted with a saturated hydrocarbon-based alkyl chain, and wherein said organic phase further comprises at least one medium which is a solvent for said polysaccharide alkyl ether; and wherein said nonaqueous cosmetic composition forms a shiny film when applied to a support.

2. A composition according to claim 1, wherein two to four hydroxyl groups per unit are substituted with said saturated hydrocarbon-based alkyl chain.

3. A composition according to claim 1, wherein said saturated hydrocarbon-based alkyl chain comprises from 1 to 24 carbon atoms.

4. A composition according to claim 3, wherein said saturated hydrocarbon-based alkyl chain comprises from 1 to 10 carbon atoms.

5. A composition according to claim 4, wherein said saturated hydrocarbon-based alkyl chain comprises from 1 to 6 carbon atoms.

6. A composition according to claim 5, wherein said saturated hydrocarbon-based alkyl chain comprises from 1 to 3 carbon atoms.

7. A composition according to claim 1, wherein said saturated hydrocarbon-based alkyl chain is a methyl, ethyl, n-propyl, isopropyl, n-butyl, isobutyl, tert-butyl, or n-pentyl radical.

8. A composition according to claim 4, wherein said hydrocarbon-based alkyl chain is a methyl, ethyl, n-propyl, isopropyl, n-butyl, isobutyl, or tert-butyl radical.

9. A composition according to claim 1, wherein said saccharide rings are mannose, galactose, glucose, furanose, rhamnose, or arabinose.

10. A composition according to claim 1, wherein said at least one polysaccharide alkyl ether is an alkyl ether of a gum.

11. A composition according to claim 10, wherein said gum is overall nonionic.

12. A composition according to claim 10, wherein said gum is a guar gum, carob gum, karaya gum, or gum tragacanth.

13. A composition according to claim 1, wherein said alkyl ether is alkyl galactomannan with a $C_1$ to $C_6$ alkyl chain.

14. A composition according to claim 13, wherein said alkyl ether is alkyl galactomannan with a $C_1$ to $C_3$ alkyl chain.

15. A composition according to claim 1, wherein said at least one polysaccharide alkyl ether is guar gum comprising an ethyl chain with a degree of substitution ranging from 2 to 3.

16. A composition according to claim 15, wherein said degree of ranges from 2.5 to 2.8.

17. A composition according to claim 1, wherein the weight ratio of said at least one medium to said at least one polysaccharide alkyl ether ranges from 5:1 to 500:1.

18. A composition according to claim 1, wherein said at least one polysaccharide alkyl ether has a weight average molecular weight ranging from greater than 200,000 to 1,000,000.

19. A composition according to claim 1, wherein said at least one polysaccharide alkyl ether is present in an amount ranging from 0.2 to 20% by weight relative to the total weight of said composition.

20. A composition according to claim 19, wherein said at least one polysaccharide alkyl ether is present in an amount ranging from 1.5 to 8% by weight relative to the total weight of said composition.

21. A composition according to claim 1, wherein said at least one film-forming polymer is a nitrocellulose, cellulose acetobutyrate, polyvinyl butyral, resin resulting from the condensation of formaldehyde with an arylsulphonamide, alkyd resin, polyester, acrylic, or polyurethane.

22. A composition according to claim 1, wherein said at least one film-forming polymer is present in an amount ranging from 0.5% to 40% by weight relative to the total weight of said composition.

23. A composition according to claim 1, wherein said solvent for said polysaccharide alkyl ether is an oil.

24. A composition according to claim 23, wherein said composition further comprises at least one complementary oil which is not a solvent for said polysaccharide alkyl ether.

25. A composition according to claim 1, wherein said composition further comprises at least one plasticizer for said at least one film-forming polymer.

26. A composition according to claim 1, wherein said composition further comprises at least one fumed silica.

27. A composition according to claim 26, wherein said at least one fumed silica is present in an amount ranging from 0.1% to 5% by weight relative to the total weight of the composition.

28. A composition according to claim 27, wherein said at least one fumed silica is present in an amount ranging from 0.5% to 1% by weight relative to the total weight of the composition.

29. A composition according to claim 1, wherein said composition further comprises at least one clay.

30. A composition according to claim 29, wherein said at least one clay is present in an amount ranging from 0.1% to 3% by weight relative to the total weight of the composition.

31. A composition according to claim 30, wherein said at least one clay is present in an amount ranging from 0.5% to 1.5% by weight relative to the total weight of the composition.

32. A nail care or nail varnish composition comprising at least one film-forming polymer and an organic phase comprising an effective thickening amount of at least one polysaccharide alkyl ether formed of units comprising at least two different saccharide rings, wherein each unit contains at least one hydroxyl group substituted with a saturated hydrocarbon-based alkyl chain, and wherein said organic phase further comprises at least one medium as a solvent for said polysaccharide alkyl ether; and wherein said nail care or nail varnish composition forms a shiny film when applied to a support.

33. A method of thickening a cosmetic composition comprising a film-forming polymer and an organic phase comprising at least one medium as a solvent comprising the step of including in said composition an effective thickening amount of at least one polysaccharide alkyl ether formed of units comprising at least two different saccharide rings, wherein each unit contains at least one hydroxyl group substituted with a saturated hydrocarbon-based alkyl chain, and further wherein said medium is a solvent for said polysaccharide alkyl ether; and wherein the thickened composition forms a shiny film when applied to a support.

34. A method according to claim 33, wherein said at least one polysaccharide alkyl ether is an alkyl ether of a guar gum, carob gum, karaya gum, gum tragacanth, or a mixture thereof.

35. A method comprising the step of applying an effective amount of at least one composition according to claim 1 to a keratinous material and/or a mucous membrane.

36. A method for cosmetically treating a keratinous material and/or a mucous membrane comprising the step of applying an effective amount of at least one composition according to claim 1 to said keratinous material and/or said mucous membrane.

37. A method according to claim 36, wherein said keratinous material is nails.

* * * * *

UNITED STATES PATENT AND TRADEMARK OFFICE
CERTIFICATE OF CORRECTION

PATENT NO. : 6,726,916 B1
DATED : April 27, 2004
INVENTOR(S) : Roland Ramin

It is certified that error appears in the above-identified patent and that said Letters Patent is hereby corrected as shown below:

Column 7,
Line 56, "of ranges" should read -- of substitution ranges --

Signed and Sealed this

Twenty-seventh Day of July, 2004

JON W. DUDAS
*Acting Director of the United States Patent and Trademark Office*